(12) United States Patent
Henschke et al.

(10) Patent No.: US 8,338,586 B2
(45) Date of Patent: Dec. 25, 2012

(54) PROCESS OF MAKING CLADRIBINE

(75) Inventors: Julian Paul Henschke, Summertown (AU); Xiaoheng Zhang, Lianyungang (CN); Chu Guodong, Jiaxiang County (CN); Lijun Mei, Taihe (CN); Yung Fa Chen, Chiali (TW)

(73) Assignee: ScinoPharm (Kunshan) Biochemical Technology Co., Ltd., Kunshan (CN)

( * ) Notice: Subject to any disclaimer, the term of this patent is extended or adjusted under 35 U.S.C. 154(b) by 0 days.

(21) Appl. No.: 13/429,827

(22) Filed: Mar. 26, 2012

(65) Prior Publication Data

US 2012/0197010 A1     Aug. 2, 2012

Related U.S. Application Data

(62) Division of application No. 12/857,939, filed on Aug. 17, 2010, now Pat. No. 8,232,387.

(60) Provisional application No. 61/234,683, filed on Aug. 18, 2009.

(51) Int. Cl.
| | |
|---|---|
| *C07H 19/00* | (2006.01) |
| *C07H 19/22* | (2006.01) |
| *A01N 43/04* | (2006.01) |
| *A61K 31/70* | (2006.01) |

(52) U.S. Cl. .................................. 536/27.11
(58) Field of Classification Search ................ None
See application file for complete search history.

(56) References Cited

U.S. PATENT DOCUMENTS

| 2002/0052491 A1 | 5/2002 | Gerszberg et al. |
| 2004/0039190 A1 | 2/2004 | Gupta et al. |
| 2008/0207891 A1 | 8/2008 | Robins et al. |

FOREIGN PATENT DOCUMENTS

| CA | 2493724 | 3/2004 |
| WO | WO 00/64918 | 11/2000 |
| WO | WO00/64918 | 11/2000 |
| WO | WO2004/018490 | 3/2004 |
| WO | WO2006/138396 | 12/2006 |

OTHER PUBLICATIONS

Lu, Youchang, et al., "Synthesis of 2'-deoxyadenosine", Applied Chemical Industry, Jul. 2006, vol. 35, No. 7, pp. 564-565 and 568.
Robins, et al., Purine Nucleosides. XI. The synthesis of 2'-Deoxy-9-α- and—β-D-ribofuranosylpurines and the Correlation of their anomeric Structure with Proton Magentic Resonance Spectra, *Journal of the American Chemical Society*, 87:21, p. 4934-4939, Nov. 5, 1965.
Kazimierczuk, et al., Synthesis of 2'-Deoxytubercidin, 2'Deoxyadenosine, and Related 2'-Deoxynucleosides via a Novel Direct Stereospecific Sodium Salt Glycosylation Procedure, *J. Am. Chem. Soc.* (1984), 106, 6379-6382.
Niedballa et al., A General Synthesis of N-Glycosides. V.[1,2] Synthesis of 5-Azacytidines, *J. Org. Chem.*, vol. 39, No. 25, p. 3672-3674 (1974).
Zhong et al., Regiospecific and Highly Stereoselective Coupling of 6-(Substituted-imidazol-1-yl)purines with 2-Deoxy-3,5-di-O-(p-toluoyl)-α-D-erythro-pentofuranosyl Chloride. Sodium-Salt Glycosylation in Binary Solvent Mixtures: Improved Synthesis of Cladribine, *J. Org. Chem.*, 71, 7773-7779 (2006).
Niedballa et al., A General synthesis of N-Glycosides. I.[1] Synthesis of Pyrimidine Nucleosides, *J. Org. Chem.*, vol. 39, No. 25, p. 3654-3660 (1974).
Christensen et al., Synthesis and Biological Activity of Selected 2,6-Disubstituted-(2-deoxy-α- and—β-D-erythro-pentofuranosyl)purines, Journal of Medicinal Chemistry, vol. 15, No. 7, p. 735-739 (1972).
Sato et al., Substituent and solvent effects of TMS Triflate Mediated C1' Epimerization of β-Thymidine to α-Thymidine, *Eur. J. Org. Chem.*, 87-93 (2002).

*Primary Examiner* — Layla Bland

(57) ABSTRACT

A method of making cladribine with an increased purity comprising:
- a) dissolving crude cladribine in a protic solvent in the presence of a base to form a solution comprising dissolved crude cladribine;
- b) maintaining the solution at an elevated temperature so that the solution is homogeneous until the amount of protected or partially protected nucleoside impurities in the solution is reduced to a pre-determined upper limit; and
- c) cooling the solution of step b) so that crystals of cladribine are formed and isolated.

6 Claims, No Drawings

PROCESS OF MAKING CLADRIBINE

RELATED APPLICATIONS

This application is a division of U.S. patent application Ser. No. 12/857,939, filed Aug. 17, 2010, now U.S. Pat. No. 8,232,387 which claims priority from U.S. Provisional Patent Application Ser. No. 61/234,683 which was filed on Aug. 18, 2009. The entire content of U.S. patent application Ser. No. 12/857,939 and U.S. Provisional Patent Application Ser. No. 61/234,683 is incorporated herein as reference.

BACKGROUND OF THE INVENTION

1. Field of the Invention

The present application relates to the synthesis of API (active pharmaceutical ingredient) grade 6-amino-2-chloro-9-(2'-deoxy-β-D-ribofuranosyl)-purine, otherwise known as cladribine (I), CdA and 2-chloro-2'-deoxyadenosine, that can be used on manufacturing scales.

2. Description of the Related Art

Previously Robins and Robins (Robins, M. J. and Robins, R. K., *J. Am. Chem. Soc.* 1965, 87, 4934-4940) reported that acid-catalyzed fusion of 1,3,5-tri-O-acety-2-deoxy-D-ribofuranose and 2,6-dichloropurine gave a 65% yield of an anomeric mixture 2,6-dichloro-9-(3',5'-di-O-acetyl-2'-deoxy-α-, β-D-ribofuranosyl)-purines from which the α-anomer was obtained as a pure crystalline product by fractional crystallization from ethanol in 32% yield and the equivalent β-anomer remained in the mother liquor (see Scheme 1). The β-anomer, which could have been used to synthesize cladribine, wasn't isolated further. The α-anomer was treated with methanolic ammonia which resulted in simultaneous deacetylation and amination to give 6-amino-2-chloro-9-(2'-deoxy-α-D-ribofuranosyl)-purine, which is a diastereomer of cladribine.

Scheme 1-Robins' 1965 Synthesis of α-anomer of Cladribine

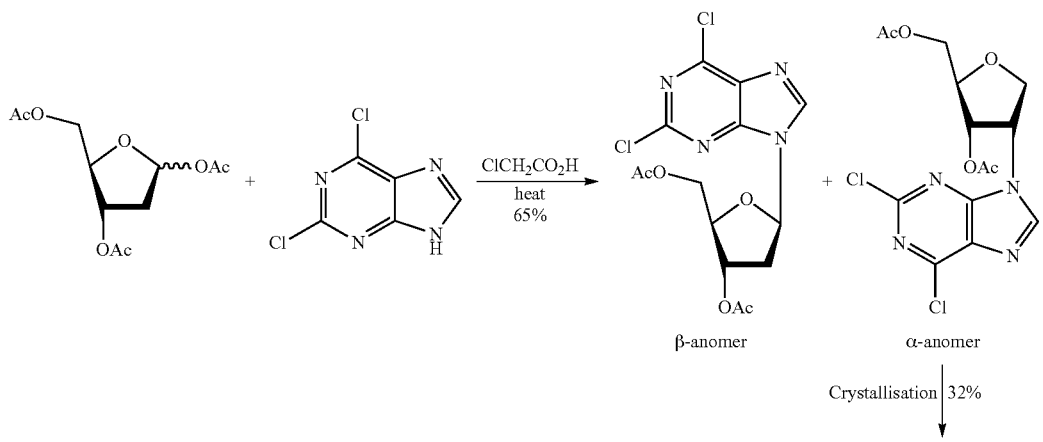

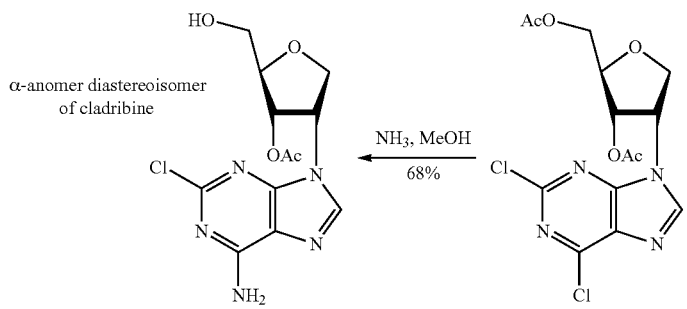

Broom et al. (Christensen, L. F., Broom, A. D., Robins, M. J., and Bloch, A., *J. Med. Chem.* 1972, 15, 735-739) adapted Robins et al.'s method by treating the acetylated mixture (viz., 2,6-dichloro-9-(3',5'-di-O-acety-2'-deoxy-α,β-D-ribofuranosyl)-purine) with liquid ammonia and reacylating the resulting 2'-deoxy-α- and -β-adenosines with p-toluoyl chloride (see Scheme 2). The desired 2-chloro-9-(3',5'-di-O-p-toluoyl-2'-deoxy-β-D-ribofuranosyl)-adenine was then separated by chromatography and removal of the p-toluoyl group resulted in cladribine in 9% overall yield based on the fusion of 1,3,5-tri-O-acety-2-deoxy-D-ribofuranose and 2,6-dichloropurine.

vided an improved method in which the sodium salt of 2,6-dichloropurine was coupled with 1-chloro-2-deoxy-3,5-di-O-p-toluoyl-α-D-ribofuranose in acetonitrile (MeCN) to give the protected β-nucleoside in 59% isolated yield, following chromatography and crystallisation, in addition to 13% of the undesired N-7 regioisomer (see Scheme 3). The apparently higher selectivity in this coupling reaction is attributed to it being a direct $S_N 2$ displacement of the chloride ion by the purine sodium salt. The protected N-9 2'-deoxy-β-nucleoside was treated with methanolic ammonia at 100° C. to give cladribine in an overall 42% yield. The drawback of this process is that the nucleophilic 7-position nitrogen competes in the $S_N 2$ reaction against the nucleophilic 9-position, lead-

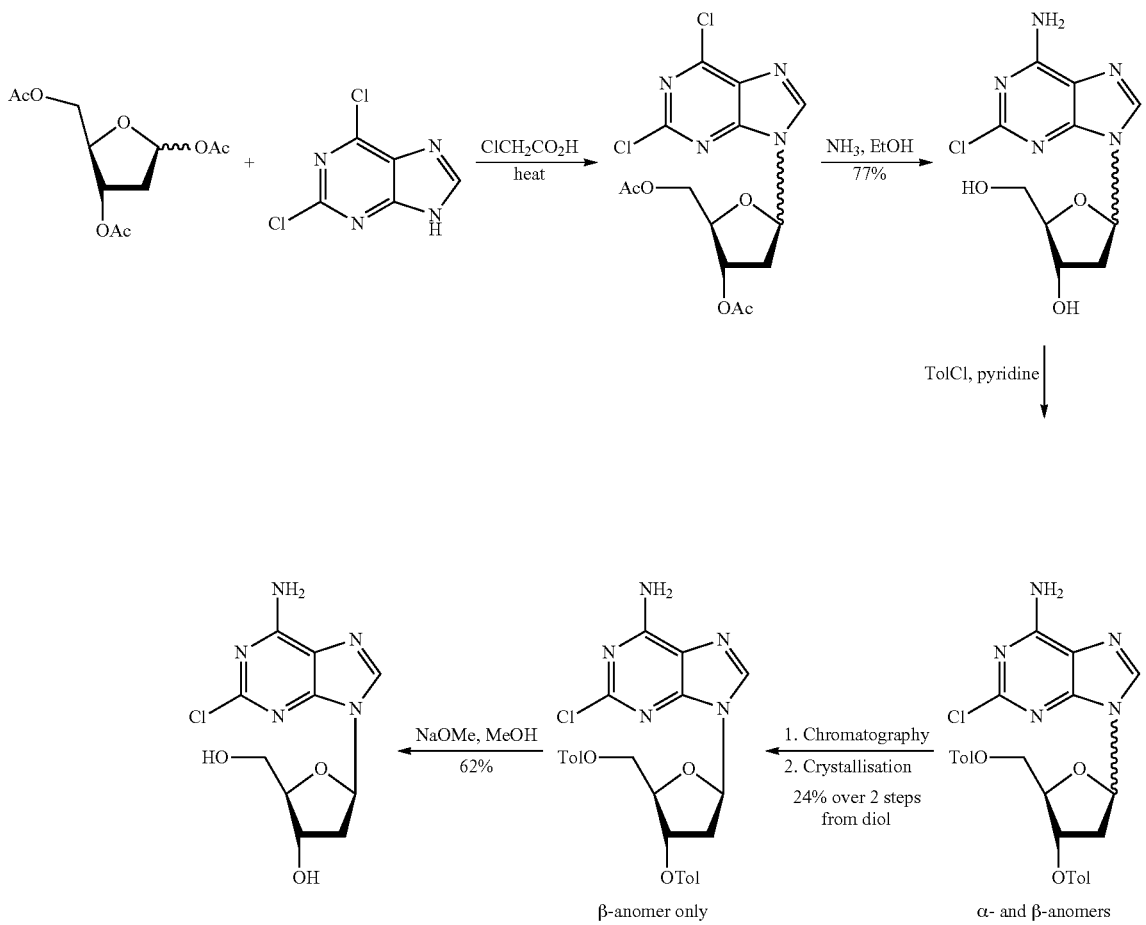

To increase the stereoselectivity in favour of the β-anomer, Robins et al. (Robins, R. L. et al., *J. Am. Chem. Soc.* 1984, 106, 6379-6382, U.S. Pat. No. 4,760,137, EP0173059) proing to a mixture of the N-7 and N-9 glycosyl isomers as well as the need for chromatography and crystallisation to obtain the pure desired isomer.

Scheme 3-Robins' $S_N2$ Approach

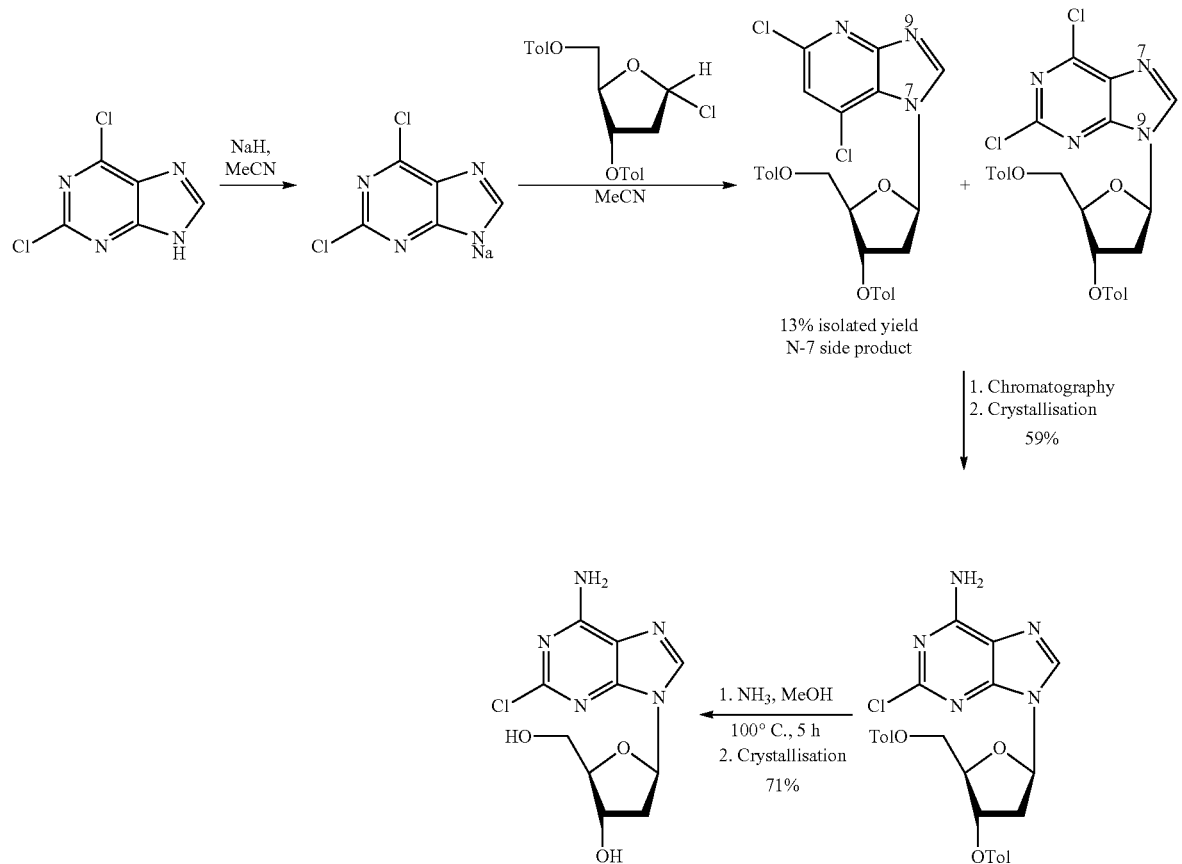

Gerszberg and Alonso (Gerszberg S, and Alonso, D. WO0064918, and US20020052491) also utilised an $S_N2$ approach with 1-chloro-2-deoxy-3,5-di-O-p-toluoyl-α-D-ribofuranose but instead coupled it with the sodium salt of 2-chloroadenine in acetone giving the desired β-anomer of the protected cladribine in 60% yield following crystallisation from ethanol (see Scheme 4). After the deprotection step using ammonia in methanol (MeOH), the β-anomer of cladribine was isolated in an overall 42% yield based on the 1-chlorosugar, and 30% if calculated based on the sodium salt since this was used in a 2.3 molar excess.

Scheme 4- Gerszberg and Alonso's cladribine synthesis

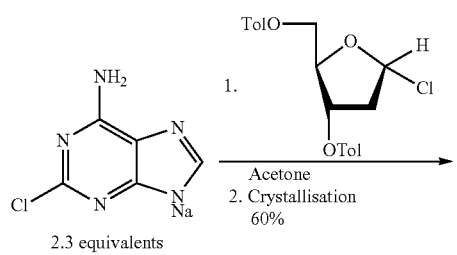

-continued

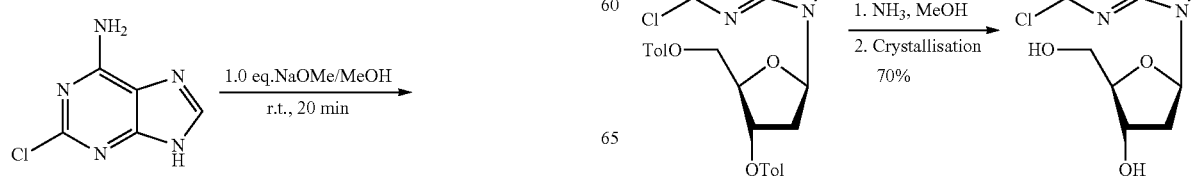

To increase the regioselectivity towards glycosylation of the N-9 position, Gupta and Munk recently (Gupta, P. K. and Munk, S. A., US20040039190, WO2004018490 and CA2493724) conducted an $S_N2$ reaction using the anomerically pure α-anomer, 1-chloro-2-deoxy-3,5-di-O-p-toluoyl-α-D-ribofuranose but coupling it with the potassium salt of a 6-heptanoylamido modified purine (see Scheme 5). The bulky alkyl group probably imparted steric hindrance around the N-7 position, resulting in the reported improved regioselectivity. Despite this, following deprotection, the overall yield of cladribine based on the 1-chlorosugar was 43%, showing no large improvement in overall yield on related methods. Moreover 2-chloroadenine required prior acylation with heptanoic anhydride at high temperature (130° C.) in 72% yield, and the coupling required cryogenic cooling (-30° C.) and the use of the strong base potassium hexamethyldisilazide and was followed by column chromatography to purify the product protected cladribine.

Scheme 5-Gupta and Munk's cladribine synthesis

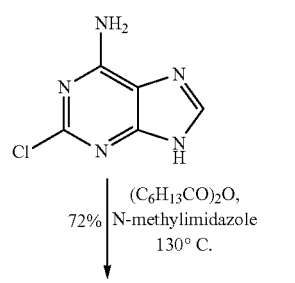

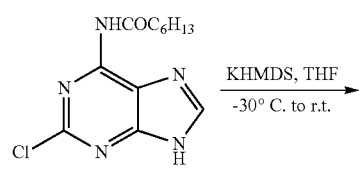

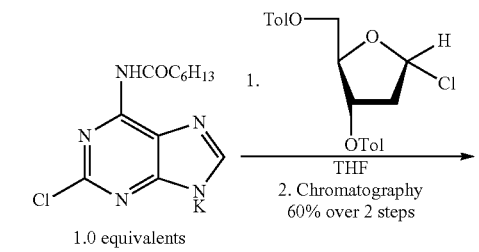

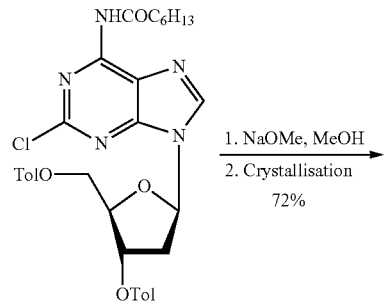

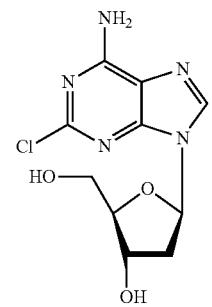

More recently Robins et al. (Robins, M. J. et al., *J. Org. Chem.* 2006, 71, 7773-7779, US20080207891) published a procedure for synthesis of cladribine that purports to achieve almost quantitative yields in the N-9-regioselective glycosylation of 6-(substituted-imidazol-1-yl)-purine sodium salts with 1-chloro-2-deoxy-3,5-di-O-p-toluoyl-α-D-ribofuranose in MeCN/dichloromethane (DCM) mixtures to give small or no detectable amounts of the undesired α-anomer (see Scheme 6). In actuality this was only demonstrated on the multi-milligram to several grams scale, and whilst the actual coupling yield following chromatography of the desired N-9-β-anomer was high (83% to quantitative), the protected 6-(substituted-imidazol-1-yl)-products were obtained in 55% to 76% yield after recrystallisation. Following this, toxic benzyl iodide was used to activate the 6-(imidazole-1-yl) groups which were then subsequently displaced by ammonia at 60-80° C. in methanolic ammonia to give cladribine in 59-70% yield following ion exchange chromatography and multiple crystallisations, or following extraction with DCM and crystallisation. Although high anomeric and regioselective glycosylation was demonstrated the procedure is longer than the prior arts, atom uneconomic and not readily applicable to industrial synthesis of cladribine such as due to the reliance on chromatography and the requirement for a pressure vessel in the substitution of the 6-(substituted-imidazole-1-yl) groups.

Scheme 6-Robins' 6-(imidazol-1-yl)-based cladribine synthesis

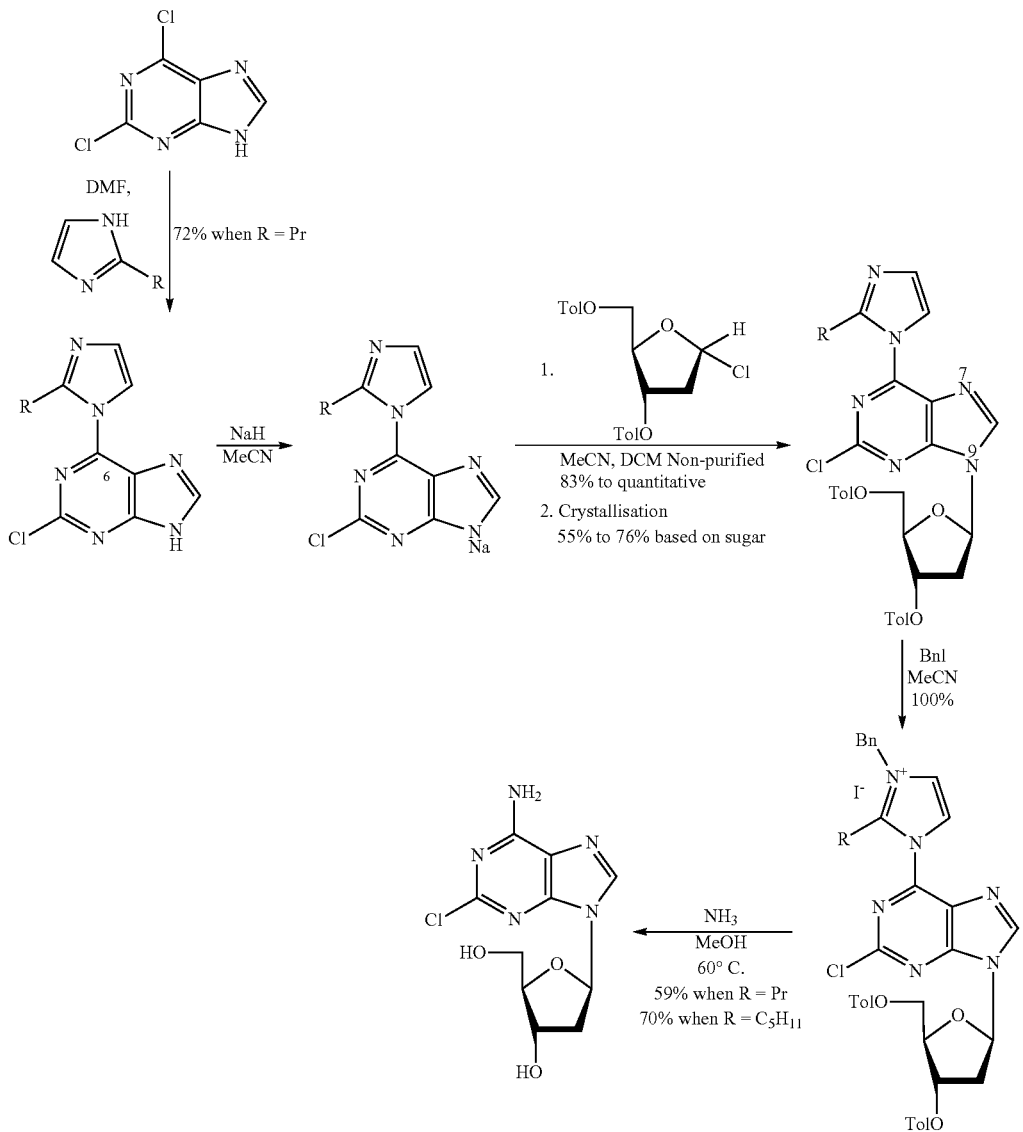

Therefore, there is a need for a more direct, less laborious process, which will produce cladribine in good yield and high purity that is applicable to industrial scales.

SUMMARY OF THE INVENTION

In accordance with one aspect of the present application, a process for making cladribine of formula I

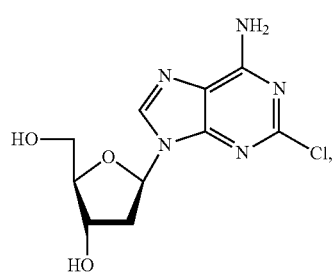

comprises:

a) coupling a compound of formula II

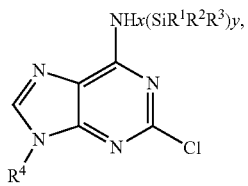

wherein each of $R^1$, $R^2$ and $R^3$ is independently alkyl, alkenyl, alkynyl or aryl, preferably, each of $R^1$, $R^2$ and $R^3$ independently has 1-20 carbon atoms, more preferably, each of $R^1$, $R^2$ and $R^3$ is methyl, x is 0, 1 or 2, y is 2, 1 or 0, and $R_4$ is hydrogen or $SiR^1R^2R^3$, with a protected 2-deoxy-ribofuranose of formula III

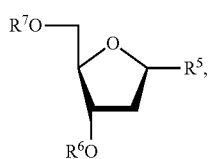

III wherein each of $R^6$ and $R^7$ is independently a hydroxyl protecting group, and $R^5$ is a leaving group, in an organic solvent to obtain a reaction mixture comprising a β-anomer of formula IV

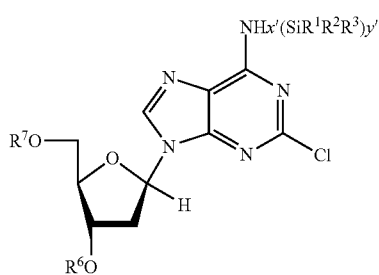

IV wherein x' is 0, 1 or 2, y' is 2, 1 or 0;
b) selectively precipitating the β-anomer of formula IV from the reaction mixture in the presence of MeCN to obtain a heterogeneous mixture;
c) isolating the precipitated β-anomer of formula IV from the heterogeneous mixture to obtain isolated and substantially enriched β-anomer of formula IV; and
d) converting the isolated and substantially enriched β-anomer of formula IV to obtain cladribine.

Preferably, the hydroxyl protecting group may be an acyl group, such as substituted or unsubstituted benzoyl group and halo-substituted aroyl group, more specifically 4-chloro-benzoyl group. The hydroxyl protecting group may also be a silyl group. $R^5$ is a leaving group that will leave from the compound of formula III during the coupling reaction so that the compound of formula II and the compound formula III reacts and forms the compound of formula IV. For example, the leaving group leaves from the compound of formula III upon activated by a Lewis acid or Brønsted acid. The leaving group may be, for example, alkoxy, aryloxy, or acyloxy (including acetoxy, benzoyloxy and substituted benzoyloxy), more preferably an acetoxy group.

The compound of formula II may be prepared by silylating 2-chloroadenine with a silylating agent in an organic solvent or neat, wherein x is 0, 1 or 2, y is 2, 1 or 0, $R_4$ is hydrogen or $SiR^1R^2R^3$, respectively, and when x is 2, y is 0, $R^4$ must be $SiR^1R^2R^3$. The compound of formula II preferably possesses at least one silyl group, more preferable at least two silyl groups. Preferably, the silylation is carried out in an organic solvent. The organic solvent may be a nitrile, an ether, a hydrocarbon (such as an aromatic hydrocarbon and a chlorinated hydrocarbon), or a silylating agent, including MeCN, THF, DCM, DCE, PhMe, HMDS, BSTFA, BSA, or a mixture of two or more of these solvents. More preferably, the organic solvent is MeCN. Preferably, the organic solvent is the same as that used in the coupling step a). The silylating agent may be BSTFA, HMDS, BSA, TMSCl, MSA, MSTFA or a mixture of at least two of these agents. More preferably, the silylating agent is BSTFA. Preferably, the silylated compound of formula II is directly used in the subsequent coupling reaction without being isolated.

The coupling step a) is carried out in the presence of a Lewis or Brønsted acid, preferably in the presence of a sulfonic acid based Lewis or Brønsted acid. Preferably, the sulfonic acid based Lewis acid is a non-metallic Lewis acid. The non-metallic Lewis or Brønsted acid used in step (a) may be TfOH, TMSOTf, TESOTf, TMSI, TBSOTf, TsOH, MsOH, $Ms_2O$, or a combination of two or more of these acids. More preferably, the acid is TfOH. The organic solvent used in the coupling step (a) is preferably MeCN. The coupling step a) may be conducted at a temperature of between about 0° C. to about reflux of the organic solvent; more preferably from 40° C. to 80° C., in particular about 60° C., so that the desired β-anomer of the protected nucleoside compound of formula IV precipitates selectively from the reaction mixture substantially free of the undesired isomers and other reaction products and impurities.

In accordance with a preferred embodiment of the present application, prior to commencing the step of c), the process as described above further comprises a step of aging the heterogeneous mixture formed in step b), i.e., maintaining the heterogeneous mixture formed in step b) at an elevated temperature, preferably 40° C. to 85° C.", more preferably at 60° C., for an extended period of time, preferably no less than 2 hours, more preferably from 6 to 24 hours.

The converting step d) may comprise deprotecting the compound of formula IV and/or removing a silyl group, if any, to make the cladribine product.

In accordance with another aspect of the present application, a process for making cladribine with an increased purity comprises:

a) dissolving crude cladribine in a protic solvent in the presence of a base to form a solution comprising dissolved crude cladribine;

b) maintaining the solution at an elevated temperature (i.e., a temperature that is higher than room temperature, preferably between 60° C. and reflux temperature of the protic solvent) so that the solution is homogeneous until the amount of protected or partially protected nucleoside impurities is reduced to a pre-determined upper limit;

c) cooling the solution of step b) so that crystals of cladribine are formed and isolated. The elevated temperature refers to a temperature that is higher than room temperature, preferably between 60° C. and reflux temperature of the protic solvent.

The protic solvent may be an aliphatic (e.g., $C_1$-$C_6$) alcohol, such as MeOH and EtOH, or a mixture of aliphatic alcohol and water. Preferably, the protic solvent is a mixture of water and methanol. The protic solvent used herein may be a mixture of two or more protic solvents. The base may be an alkoxide, hydroxide, carbonate, ammonia, or amine, and preferably, sodium methoxide.

Preferably, the pre-determined upper limit of the amount of protected or partially protected nucleoside impurities may be 0.10% by HPLC analysis of the solution.

The isolated cladribine mentioned above may be further recrystallized from, e.g., an aliphatic alcohol and water.

In accordance with yet another aspect of the present application, a process of making a compound of formula IV

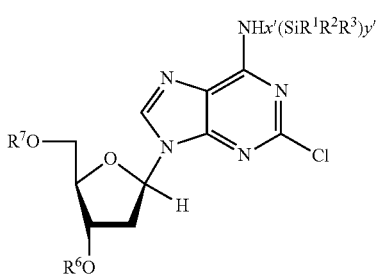

wherein each of $R^1$, $R^2$ and $R^3$ is independently alkyl, alkenyl, alkynyl or aryl (e.g., $C_1$ to $C_{20}$), x' is 0, 1 or 2, y' is 2, 1 or 0, and each of $R^6$ and $R^7$ is independently a hydroxyl protecting group, with an improved purity, comprises:

(a) treating a mixture comprising the compound of formula IV and at least one undesired isomer with a sulfonic acid based Lewis or Brønsted acid in an organic solvent and in the presence of a silylating agent (preferably BSTFA) so that the at least one undesired isomer isomerizes and converts to the compound of formula IV; and (b) isolating the compound of formula IV from the mixture of step (a).

The organic solvent may be a nitrile, an ether, a hydrocarbon, an aromatic hydrocarbon, a chlorinated hydrocarbon, or a silylating agent, including MeCN, THF, DCM, DCE, PhMe, HMDS, BSTFA, BSA, or a mixture of two or more of these solvents. More preferably, the organic solvent is MeCN.

The catalyst is preferably TfOH or TMSOTf. The compound of formula IV to be purified may be contaminated with undesired alpha-anomeric isomer (e.g., compound of formula V shown below) and/or N-7 regioisomers (e.g., compounds of formula VI and VII shown below).

The mixture comprising the compound of formula IV may also be obtained by treating a non-silylated derivative compound of formula IV (i.e., wherein x'=2 and y'=0) with a silylating agent (preferably BSTFA), preferably in molar excess with respect to non-silylated derivative compound of formula IV, in an organic solvent (preferably MeCN), preferably without subsequent isolation of the compound of formula IV from the organic solvent.

The compound of formula IV with an improved purity obtained in accordance with the present application may be further converted to cladribine by, e.g., removing the protecting and/or silyl groups, if any.

In accordance with a further aspect of the present application, a process of making a compound of formula IV as defined above (i.e., each of $R^1$, $R^2$ and $R^3$ is independently alkyl, alkenyl, alkynyl or aryl, x' is 0, 1 or 2, y' is 2, 1 or 0, and each of $R^6$ and $R^7$ is independently a hydroxyl protecting group) comprises coupling a compound of formula II as defined above with a protected 2-deoxy-ribofuranose of formula III as defined above in an organic solvent and in the presence of a sulfonic acid based Lewis or Brønsted acid to obtain the compound of formula IV, which may be further converted to cladribine. The organic solvent may be an organic nitrile, aromatic compound, chlorinated compound, ether, hydrocarbon or a mixture of two or more of these compounds. Preferably, the organic solvent may be MeCN, PhMe, DCM, THF, or a mixture of two or more of these compounds.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

As used herein, the term "enriched β-anomer" (beta anomer) refers to a nucleoside product that comprises more than 1:1, preferably at least 2:1, more preferably at least 3:1 of β-anomer/its corresponding α-anomer (alpha anomer).

As used herein, the term "substantially enriched β-anomer" refers to a nucleoside product that comprises more than 10:1, preferably at least 20:1, more preferably about 40:1 of β-anomer/its corresponding α-anomer.

As used herein, the term "aging" refers to maintaining a reaction mixture for an extended period of time, e.g., at least 2 hours, preferably 6 to 24 hours, at an elevated temperature (i.e., higher than room temperature), preferably about 40° C. to 80° C., more preferably about 60° C. More preferably, during the aging, the reaction mixture is maintained under the same or substantially the same conditions (e.g., temperature, solute concentration, catalyst amount) of the immediately preceding reaction, e.g., coupling reaction discussed above, after the immediately preceding reaction is completed. For example, the conditions of the immediately preceding reaction are not interfered or changed during the aging step. As discussed more detail below, the aging leads to a higher isolated yield of desired β-anomer than one would otherwise expect without using the aging step.

The present application relates to the synthesis of cladribine (I) (see, e.g., Scheme 7 below).

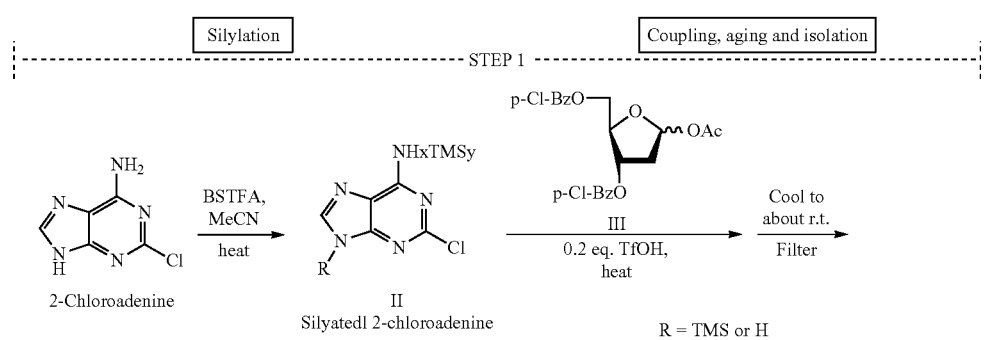

Scheme 7 - synthesis of cladribine in accordance with a preferred embodiment of the present application

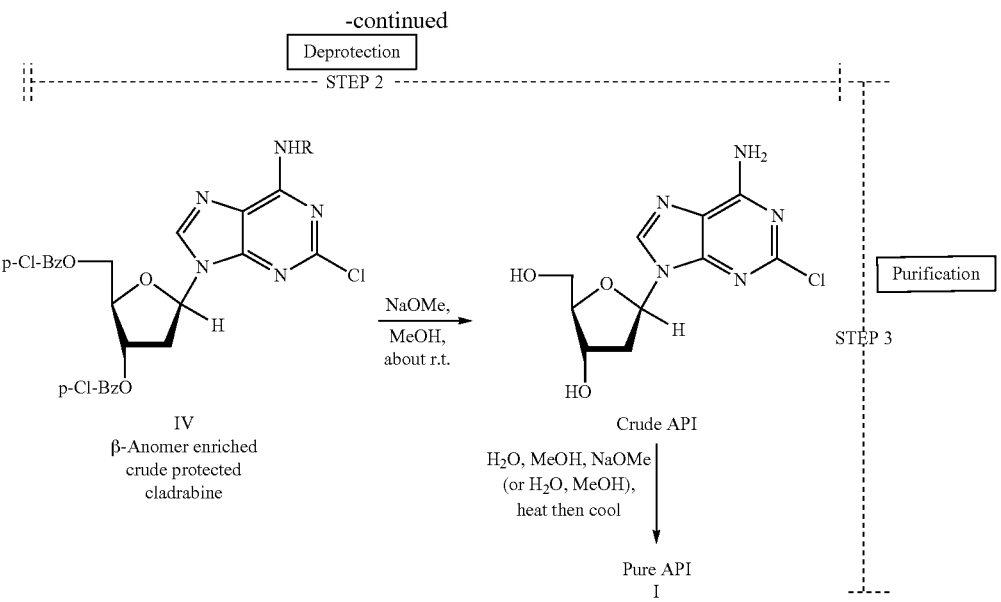

Cladribine is prepared by direct coupling of tri-O-protected 2-deoxy-ribofuranose III with silylated, preferably doubly silylated, 2-chloroadenine (II, silylated 2-chloro-6-aminopurine) catalysed by Brønsted acids, mostly preferably derived from sulfonic acids, or non-metallic Lewis acids mostly preferably derived from sulfonic acids, such as trimethyl silyl esters of sulfonic acids. During the coupling reaction step and after it is complete in an aging step an overall enrichment in the amount of the desired β-anomer of the N-9-glycosylated product occurs, which is believed to be due to an unreported isomerisation of the undesired α-anomer V of the N-9-glycosylated product into the desired β-anomer IV of the N-9-glycosylated (formulas of these anomers are shown below), which then precipitates from the reaction mixture. The silylation, coupling, and aging steps can be carried out in one reaction vessel allowing for a very efficient process. The coupling reaction is catalysed by a substoichiometric amount of catalyst, and due to the nature of the catalyst, its small amount and the precipitation of the desired β-anomer IV of the protected N-9-glycosylated product from the reaction mixture, a subsequent catalyst deactivation step is not required. The lack of a catalyst deactivation step is an advantage for the manufacture of cladribine because it avoids the need for an aqueous work-up, which would, otherwise increases the operation time in the manufacturing plant. The isolated N-silyl, di-O-acyl protected product Iva is subjected to deprotection in a separate step to produce cladribine in a good yield and a high purity. The high anomeric and regio purity of the protected product IV means that no purification step is required. The coupling stage proceeds with the addition of only tri-O-protected 2-deoxy-ribofuranose III and a catalyst to the silylated 2-chloroadenine II, with no other processing step (i.e., no work-up, aqueous work-up, catalyst deactivation/quench, distillation or reagent transfers) being required. The desired protected β-anomer IV of the N-9-glycosylated nucleoside can be directly isolated as a solid from the coupling reaction mixture by filtration in a high purity and yield, and it does not require subsequent purification. The β-anomer IV is isolated in a higher yield and with a very low amount of the α-anomer V than expected. This is very favourable because analytical data shows that the coupling anomeric selectivity is low.

Thus, by selection of conditions under which the α-anomer is dissolved in solution but in which the desired β-anomer is not dissolved, along with consumption of the α-anomer V including by isomerisation occurring in solution and the resultant desired protected β-anomer precipitating, an overall high selectivity is observed. In this manner, some of the α-anomer V formed in the coupling reaction can be converted into the desired β-anomer. By the end of the aging step, the amount of the α-anomer in both the solid and liquid phases of the reaction is low by comparison to that of the β-anomer. The N-7 regioisomers VI and VII are not problematic because under the reaction conditions they can isomerise to the more thermodynamically stable N-9-isomers. The isolated protected β-anomer of the nucleoside is deprotected to give crude cladribine of a good purity in a high yield. Pure cladribine for human use may be obtained by an additional crystallization step. The overall yield of API grade product (HPLC purity >99.5% and no individual impurities >0.1%) is up to about 55%.

Protected nucleosides isomers

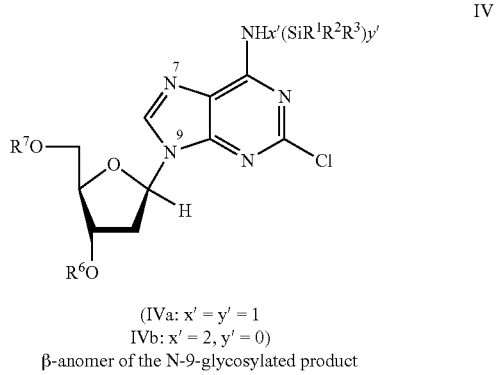

(IVa: x' = y' = 1
IVb: x' = 2, y' = 0)
β-anomer of the N-9-glycosylated product

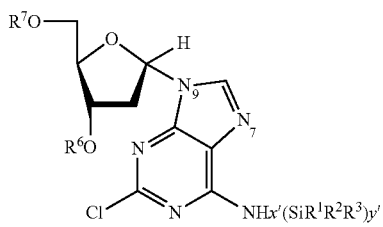

(Va: x' = y' = 1
Vb: x' = 2, y' = 0)
α-anomer of the N-9-glycosylated product

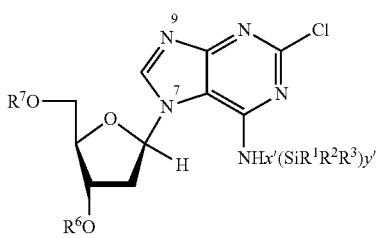

β-anomer of the N-7-glycosylated product

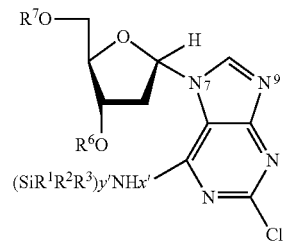

α-anomer of the N-7-glycosylated product $R^6, R^7$ = 4-Chlorobenzoyl;
x' = 0, 1 or 2,
y' = 2, 1, or 0

The silylation, coupling, aging and precipitation discussed herein may be carried out in one pot. After the coupling and aging step, the desired N-9-glycosylated β-anomer (IV) of the nucleoside is directly isolated, as a solid from the coupling reaction mixture by filtration in a relatively high purity (typically no less than 95% HPLC purity) and yield, and it does not require purification. This protected nucleoside is deprotected to give crude cladribine of a good purity in a high yield. Pure cladribine for human use may be obtained by one additional step of crystallization. The overall yield can be about 55% (unless explicitly defined otherwise, the yield described here and below is calculated from moles of starting materials and moles of product, i.e., yield=(moles of product/moles of starting materials)*100.)

We surprisingly discovered that the stereochemical isomerization of α-anomer to β-anomer could occur under the coupling step reaction conditions of the present application. More importantly, we discovered that this isomerisation process could be harnessed to provide a higher yield of the desired product IV and higher β-anomer to α-anomer ratio in the reaction product mixture, than would otherwise be provided in the coupling reaction by the appropriate selection of conditions in which the desired β-isomer is appreciably precipitated from the reaction solution but in which the undesired α-isomer does not precipitate substantially. This isomerisation and precipitation provide a higher yield, and more so when the coupling step is followed by an aging step, and purity of the desired N-9-β-anomer when isolated by direct filtration of the product mixture than would be possible by either i) direct work-up of the complete product mixture (i.e., solid and liquid phases) or, ii) under conditions in which the coupling reaction was conducted under homogeneous conditions.

It was also discovered that the undesired N-7 regioisomers VI and VII that can also form in the coupling reaction are not problematic because under the selected coupling and aging reaction conditions of the present invention can readily isomerise to the more thermodynamically stable N-9-isomers. This means that the reaction yield is not reduced by these unwanted regioisomers. This "one-pot" sequence is followed by a very simple solid product isolation by filtration of the highly enriched desired N-9-glycosylated β-anomer protected nucleoside IV which is only contaminated with a small amount of the α-anomer. Pure cladribine is obtained by deprotection and crystallisation, and the low amount of isomers and impurities formed in the key reaction sequence that precipitate with IV do not compromise the quality of the final API.

In this invention no chromatography, or fractional crystallisation as an independent operation, is required to obtain the highly enriched desired N-9-glycosylated β-anomer protected nucleoside IV, because the desired β-anomer selectively precipitates from the glycosylation reaction product mixture during the coupling reaction and during the aging step in a substantially pure form. In the preferred embodiment of this invention the purity of the precipitated IVa as measured by HPLC analysis is more than 90%, typically more than 95%. Further product IVa also precipitates from the reaction product mixture when it is cooled from the reaction temperature to about ambient temperature. Due to stereoisomerization of the anomeric stereogenic centre of the α-anomer to the less soluble β-anomer during the reaction and during the aging step, more β-anomer is formed than is otherwise formed in the coupling reaction itself. That is, although the actual anomeric selectivity of the coupling reaction is low (about 1:1 to about 2:1) under the conditions disclosed in this invention, this precipitation and isomerisation phenomenon leads to overall enrichment of the β-anomer within the total reaction system leading to ratios of more than about 2.4:1, even as high as about 3:1 or even higher, as calculated based on the whole reaction system. The β-anomer to α-anomer ratio of the isolated precipitated product IV can be as high as about 40:1. Moreover, after the ribofuranose starting material III is consumed in the coupling step, it is preferred that the mixture is heated at an elevated temperature for longer in what we refer to as the aging step, preferably at about 60° C., to improve the overall yield of the desired β-anomer. The time at which the aging step is stopped can be judged by measuring the assay (weight percent) of the undesired α-anomer V in the solution phase of the product mixture. Typically the aging step is conducted for at least 6 hours up to about 24 hours, but the length of time required for the optimum yield depends on the reaction conditions (e.g., solute concentration, temperature and amount of catalyst) and can be determined by monitoring the amount of undesired α-anomer in the solution phase.

The choice of solvent is important for this process. While a number of organic solvents may be effective, most preferred is MeCN. The amount of MeCN solvent used with respect to the nucleobase II and 2-deoxy-ribose derivative III can be selected over a range, but about 12 to about 20 volumes/weight (based on 2-chloroadenine) is preferred and about 12 to about 14 volumes/weight is most preferred. If too little MeCN is used the 2-chloroadenine does not dissolve completely in the silyation step. If a solvent that does not possess some of the desired physical characteristics of MeCN is selected, then the enrichment and the convenient isolation by filtration of the β-anomer can be difficult and/or inefficient.

Thus this very convenient process developed by the inventors was very unexpected at the outset of the research. The process is very selective for the desired β-isomer IV, even though potentially four isomers (viz., the α- and β-anomers of the N-7-glycosylated product VI and VII as well as the α- and β-anomers of the N-9-glycosylated product IV and V) may form during the coupling reaction. A temperature in excess of about 0° C., in particular a temperature of about 60° C. is preferred for the coupling reaction.

2-Chloroadenine can be silylated with a silylating agent such as N,O-bis(trimethylsilyl)trifluoroacetamide (BSTFA), N,O-bis(trimethylsilyl)acetamide (BSA), trimethylsilyl chloride (TMSCl), tert-butyl-dimethylsilyl chloride (TBSCl), TMSOTf, tert-butyl-dimethylsilyl triflate (TBSOTf) and hexamethyldisilazane, bis(trimethylsilyl)sulfate, tert-butylchlorodimethylsilane, butyl(chloro)dimethylsilane, 1-(tert-butyldimethylsilyl)imidazole, tert-butyl(chloro)diphenylsilane, N-tert-butyldimethylsilyl-N-methyltrifluoroacetamide, N,O-bis(trimethylsilyl)trifluoroacetamide, 1,3-dimethyl-1,1,3,3-tetraphenyldisilazane, 1,1,3,3-tetramethyl-1,3-diphenyldisilazane, 1,1,3,3-tetramethyl-1,3-divinyldisilazane, N-methyl-N-trimethylsilylacetamide, N-methyl-N-(trimethylsilyl)trifluoroacetamide (MSTFA), chlorotriisopropylsilane, chlorotriethylsilane, N-(trimethylsilyl)acetamidesilane, however, BSTFA is preferred when the silylation reaction is conducted in MeCN and is used in molar excess with respect to 2-chloroadenine. Although the molar excess of BSTFA can be greater than 2.0 equivalents, about 3 equivalents is preferred. When BSTFA or BSA was used to silylate 2-chloroadenine in MeCN it was discovered by GCMS analysis that the 2-chloroadenine was doubly silylated and the total ion current (TIC) chromatogram suggested the existence of only one isomer of the doubly silylated 2-chloroadenine.

For convenience and efficiency it is preferred that the silyation step is carried out in the same solvent as is used in the coupling reaction step, although these steps can be carried out in different solvents or solvent mixtures. The silyation and coupling step can be conducted in the same single reaction vessel, or in separate vessels if a filtration operation is required following the silyation step. If silylating agents other than BSTFA are used that produce a reactive by-product that interferes with the integrity of the coupling step, then the silylated product II can be purified by its isolation by methods known to those experience in the art such as including crystallisation, precipitation or solvent evaporation to provide a residue or distillation. A range of solvents can be used in the coupling step such a tetrahydrofuran (THF), toluene (PhMe), DCE (dichloroethane), HMDS, and DCM, but MeCN is preferred.

The silylated 2-chloroadenine II couples with a protected 2-deoxy-ribofuranose III in an organic solvent and in the presence of a sulfonic acid based non-metallic Lewis or Brønsted acid, including trimethylsilyl triflate (TMSOTf), TBSOTf, triethylsilyl triflate (TESOTf), triflic acid (TfOH), methanesulfonic acid (MsOH), para-toluenesulfonic acid (TsOH), triflic acid anhydride ($Tf_2O$), and methanesulfonic acid anhydride ($Ms_2O$), but preferably TfOH. Other Lewis or Brønsted acids, such as those known to those of experience in the art of nucleoside coupling reactions, can be used, but these are less preferred. The present invention is conducted preferably using a low substoichiometric amount of the coupling catalyst and most preferably about 0.2 molar equivalent (eq.) with respect to the protected 2-deoxy-ribofuranose III.

Without being bound by theory, it is believed that the coupling reaction proceeds through an $S_N1$ reaction mechanism to give an anomeric mixture of protected nucleoside products, because the ratio of the anomeric protected nucleoside products IV and V is independent of the ratio of the original anomeric mixture of the protected 2-deoxy-ribofuranose III. Thus, no special requirement for an anomerically pure starting material III is required. This is advantageous, because the non-anomerically pure starting material III can be produced more cheaply. This contrasts with other prior art methods for synthesising cladribine, such as those shown in schemes 3-6, which utilise an anomerically pure carbohydrate starting material.

In another embodiment of this invention, mixtures of coupled nucleoside products obtained via other synthetic methods can be converted to cladribine by silyation and isomerisation/precipitation followed by deprotection as described in this invention. Illustrative of this, a 50 g sample of crude non-silylated nucleoside mixture containing 58.6% (equivalent to 29.3 g) of N-9-glycosylated α-anomer Vb and 34.3% (equivalent to 17.15 g) of the N-9-glycosylated β-anomer IVb was treated with 3 molar equivalents of BSTFA in MeCN at 60° C. for 3 h directly followed by the addition of 0.2 molar equivalents TfOH with heating at 60° C. for 15 hours. The precipitated solid was filtered and dried to give 24.0 g of 95% purity precipitated IV, mostly silylated (i.e., IVa), whose composition was equivalent to 20.55 g of non-silylated IVb. Furthermore, more IV was detected in the mother liquors. Thus, in total we obtained 24% more N-9-glycosylated β-anomer IV than was put into the isomerisation reaction, of which 16% more than was put into the isomerisation reaction was isolated in the precipitation and filtration process.

Thus, while a variety of conditions may presumably be employed in this invention, the most preferred conditions are the use of MeCN as a reaction solvent, BSTFA as a silylating agent and TfOH as a catalyst and that the silyation, coupling reaction and aging step are conducted in the same vessel at about 60° C. On manufacturing scales when making cladribine for human consumption, it is preferable that the silylated product is filtered through a filter aid, but no other additional operation is required. This reaction system favours the N-9-β-anomer IV over that of the α-anomer V due to precipitation of the desired N-9-β-anomer from the coupling reaction mixture with in situ isomerisation of the unwanted N-9-α-anomer to the wanted N-9-β-anomer which precipitates from the reaction mixture. This silyation, coupling and aging reaction sequence gives about a 60-65% yield (calculated from the protected 2-deoxy-ribose starting material III) on gram up to multi-kilogram manufacturing scales of isolated solid of the substantially and satisfactorily pure N-9-β-anomer.

Direct analysis of the reaction solution by HPLC shows the actual coupling reaction without the aging step produces an approximately <1:1 to >2:1 molar ratio of the N-9-β-anomer IV/N-9-α-anomer V depending on the reaction conditions. When non-preferred silylating agents and non-preferred catalysts are used, such as BSA and $Tf_2O$, for example, we found that the selectivity can be low or even the undesired α-anomer can be favoured of the desired β-anomer. We found that the selectivity in the coupling reaction was higher when BSTFA (up to about 2.3:1 molar ratio of the N-9-β-anomer/N-9-α-anomer), rather than BSA (about 1:1 molar ratio of the N-9-β-anomer/N-9-α-anomer), was used as the silylating agent, and TfOH was used as the catalyst in MeCN when the silylating reaction product solution was directly used in the coupling step without isolation of the compound of formula II or work-up. After the aging step, the β-anomer to α-anomer ratio of the total reaction system can be more than about 2.6:1, even as high as about 3:1 or even higher, and the β-anomer to α-anomer ratio of the isolated precipitated product IV can be as high as about 40:1.

In a preferred embodiment of the invention the deprotection reaction of the compound of formula IV is conducted as a heterogeneous mixture in MeOH at about 25° C. using an alkoxide base, preferably sodium methoxide. The crude cladribine is preferably directly isolated by filtration providing a high chemical purity of typically about 96% to about 99%. Without being bound by theory, it is believed that the high purity of the crude cladribine is due to a crystallisation phenomenon of cladribine that occurs during the reaction, which was supported by X-ray powder diffraction (XRPD) analysis. The amount of MeOH solvent can be varied but about 5 volume/weight with respect to the compound of formula IV is preferred.

The inventors discovered that when the deprotection reaction was conducted under the preferred conditions of this invention, crude cladribine of high chemical purity of about 96% to about 99% by HPLC analysis was obtained. It was found, however, that the crude cladribine was sometimes contaminated with small amounts of residual IVb, Vb and partially deprotected intermediates and impurities. The inventors discovered that these impurities were very difficult to efficiently remove by a single crystallisation step from alcohols or alcohol and water solvent mixtures, and sometimes the purity criterion of isolated cladribine did not meet that of the ICH guidelines on impurities. Therefore, the inventors devised a protocol that allowed the impurities to be effectively removed. This protocol was efficiently combined with the crystallisation process, which was very convenient on manufacturing scales, and provided pure cladribine more efficiently than if separate operations were required. The combined protocol is a preferred embodiment of this invention and consists of dissolving the crude cladribine in a MeOH and water solution that contained small amount of a water soluble base, preferably sodium methoxide, wherein the amount of the base was directly related to the amount of the afore mentioned residual intermediates, isomers and impurities and partially deprotected intermediates. The mixture was conveniently heated to about reflux to dissolve the solids, and optionally cooled to about 70° C. or remaining at about reflux, and stirred at the same temperature until the aforementioned residual compounds were consumed to less than or equal to 0.10% by HPLC analysis. The cladribine was then allowed to crystallise from the solution and was isolated by filtration, washed and dried giving high purity cladribine. Although a range of weight ratios of MeOH and water could be used in this purification/crystallisation step, an approximately 4:5 weight/weight ratio, respectively, was preferred. In total an about 9:1 weight/weight ratio of the MeOH and water mixture with respect to crude cladribine was preferred. This protocol can be conducted in one reaction vessel making it very convenient. In another embodiment of this invention, optionally following this protocol a recrystallisation of the cladribine from MeOH and water can be conducted.

In the formulae (II) and (IV) described above, x and x', and y and y' are not necessarily the same. α-anomer V may lose its silyl group readily upon isolation. Water treatment or acidic water treatment or other desilylating conditions may also result in removal of the silyl groups. Compared to other protecting groups, the silyl groups are not so strongly attached to the compounds. For example, x'=1 and y'=1, the isolated compound of formula (IV) may remain the same when the "isolation" is direct filtration. If water contact step or other desilylating conditions are involved before or during the precipitating step, the compound of formula (IV) with x'=1 and y'=1 initially may be subsequently "isolated" as a compound of formula (IV) with x'=2 and y'=0.

The advantages of this invention for the synthesis include that it is applicable for manufacturing scale synthesis of API grade cladribine that is fit for human consumption. The synthetic process is efficient as demonstrated by a high overall yield, as compared to the yields of competing processes disclosed in the prior arts. The process is very convenient to operate on laboratory and manufacturing plant scales and demonstrated by multi-kilogram exemplification as disclosed in the examples below. The synthetic approach described as the preferred embodiment of this invention does not require the protected 2-deoxy-ribose III to be anomerically pure since the anomerically purity of this starting material has no relationship to the anomeric purity of the coupled nucleoside product. This reduces the cost of the starting material input. That the silylation, coupling and aging steps can be conducted in one reaction vessel, or in no more than two if a filtration step is required following the silylation step, is very advantageous. The unique utilisation of the epimerisation behaviour of the protected cladribine in conjunction with the appropriate choice of reaction conditions under which the desired β-anomer precipitates from solution but under which the undesired α-anomer remains in solution provides an improved yield of cladribine. Moreover, the appropriate choice of reaction conditions allowed the desired β-anomer of protected cladribine to precipitate from solution is such high purity that it could be isolated by filtration and used directly to make API grade cladribine without its purification. The use of non-metallic Lewis acids such as TMSOTf or Brønsted acids avoids contamination of the API product with metallic residues, which can be a problem when some metallic catalysts are used in nucleoside synthesis. Because the product of the coupling and aging step was directly isolated by filtration of the product mixture, no aqueous work up was required which improved the time efficiency of the overall process.

In one embodiment of this invention, cladribine is synthesised having API grade that is applicable on manufacturing scales as follows:

i) 2-Chloradenine is silylated using a molar excess of BSTFA in MeCN under reflux, which following completion is optionally hot (about 55° C.) filtered through a filter aid.

ii) A substoichiometric amount of TfOH is then directly added to the product solution of step (i) followed by 1-O-acetyl-3,5-di-O-(4-chlorobenzoyl)-2-deoxy-D-ribofuranose and the mixture is heated at about 60° C. for a period of hours.

iii) Following consumption of 1-O-acetyl-3,5-di-O-(4-chlorobenzoyl)-2-deoxy-D-ribofuranose the mixture is aged under approximately the same conditions as in step (ii) until the weight percent of 2-chloro-6-amino-9-[3,5-di-O-(4-chlorobenzoyl)-2'-deoxy-α-D-ribofuranosyl]-purine (Vb; α-anomer), which is detected as its non-silylated derivative in the solution phase, is less than or equal to 3%.

iv) The product mixture is then cooled to about 15 to 30° C. and then stirred for no less than 2 hours, and is then filtered to collect the solid product which is optionally washed with MeCN, and the solid is then dried to give substantially 2-chloro-6-trimethylsilylamino-9-[3,5-di-O-(4-chlorobenzoyl)-2-deoxy-β-D-ribofuranosyl]-purine (IVa).

v) The dry solid product of step (iv) was deprotected by treatment with sodium methoxide in MeOH preferably as a heterogeneous mixture at about 20 to 30° C.

vi) The product mixture of step (v) was then filtered to collect the solid product and was washed with MeOH and dried to give crude cladribine.

vii) The crude cladribine of step (vi) is purified by adding it to a mixture of water, MeOH and sodium methoxide (where the amount of sodium methoxide is determined based on the amount of residual IVb, Vb and partially deprotected intermediates and impurities remaining from the deprotection step) and heating to about reflux to dissolve, and optionally cooling to about 70° C., and stirring at the same temperature until residual impurities were consumed to less than or equal to 0.10%.

viii) The purified product mixture of step (vii) was optionally treating with activated carbon at about 65° C., hot filtered and rising with preheated MeOH and water. The product of step (vii) or the optionally carbon treated product was cooled to allow it to crystallise. The slurry formed upon crystallisation is cooled to about 10-20° C. stirred for not less than 2 hours, and is then filtered, washed with MeOH and dried providing high purity cladribine.

ix) Optionally, the isolated cladribine of step (viii) can be recrystallised by dissolving it in a mixture of water and MeOH at about reflux, and cooling to allow crystallisation. The slurry formed upon crystallisation is cooled to about 15° C. stirred for not less than 2 hours, and is then filtered, washed with MeOH and dried providing high purity cladribine.

The following examples are provided for the purpose of further illustration only and are not intended to be limitations on the disclosed invention.

EXAMPLE 1

Preparation of 2-chloro-6-trimethylsilylamino-9-[3,5-di-O-(4-chlorobenzoyl)-2-deoxy-β-D-ribofuranosyl]-purine 2-Chloroadenine (75 g, 0.44 mol, 1.0 eq.), MeCN (900 mL, 12 P), and BSTFA (343.5 g, 1.33 mol, 3.0 eq.) were stirred and heated under reflux until the mixture was almost turned clear. The mixture was cooled to 60° C. and TfOH (7.9 mL, 0.089 mol, 0.2 eq.) and then 1-O-acetyl-3,5-di-O-(4-chlorobenzoyl)-2-deoxy-D-ribofuranose (III; 200.6 g, 1.0 eq.) were added into the mixture, and then the mixture was stirred at 60° C. After 1 hour, some solid precipitated from the solution and the mixture was heated for at least a further 10 hours. The mixture was cooled to r.t. and stirred for 2 hours. The solid was filtered and dried in vacuo at 60° C. to give 180.6 g in 64% yield of a mixture of 2-chloro-6-trimethylsilylamino-9-[3,5-di-O-(4-chlorobenzoyl)-2-deoxy-β-D-ribofuranosyl]-purine (IVa) with 95.4% HPLC purity and its non-silylated derivative 2-chloro-6-amino-9-[3,5-di-O-(4-chlorobenzoyl)-2'-deoxy-β-D-ribofuranosyl]-purine (IVb) with 1.1% HPLC purity.

EXAMPLE 2

Preparation of 2-chloro-6-trimethylsilylamino-9-[3,5-di-O-(4-chlorobenzoyl)-2-deoxy-β-D-ribofuranosyl]-purine by Isomerisation of a Mixture of 2-chloro-6-amino-9-[3,5-di-O-(4-chlorobenzoyl)-2-deoxy-α,β-D-ribofuranosyl]-purine mixture 50.0 g of 2-chloro-6-amino-9-[3,5-di-O-(4-chlorobenzoyl)-2-deoxy-α,β-D-ribofuranosyl]-purine as a 0.6:1.0 mixture of the β-anomer IVb and α-anomer Vb (83.16 mmol, assay of α-anomer was 58.6% (52.06 mmol) and β-anomer was 34.3% (31.10 mmol, 17.15 g)), 68.6 g BSTFA (266.5 mmol) and 180 mL of MeCN (3.6 P) were charged into a dried 4-necked flask. The mixture was heated to 60° C. under $N_2$ for about 3 h and then 2.67 g of TfOH (17.8 mmol) was added. The mixture was stirred at 60° C. for 15 h and was then cooled to about 25° C. and stirred for a further 2 h, and then filtered. The filter cake was washed twice with MeCN (20 mL each) and dried at 60° C. in vacuo for 6 h to give 24 g of off-white solid (the assay of 2-chloro-6-amino-9-[3,5-di-O-(4-chlorobenzoyl)-2-deoxy-α-D-ribofuranosyl]-purine was 1.4% (0.60 mmol, 0.34 g), 2-chloro-6-amino-9-[3,5-di-O-(4-chlorobenzoyl)-2-deoxy-β-D-ribofuranosyl]-purine was 8.4% (3.18 mmol, 2.02 g) and 2-chloro-6-trimethylsilylamino-9-[3,5-di-O-(4-chlorobenzoyl)-2-deoxy-β-D-ribofuranosyl]-purine was 86.6% (32.73 mmol, 20.78 g)).

Analysis of the 274.8 g of the mother liquor by assay showed that it in addition to the α-anomer it contained 0.5% (1.37 g, 2.43 mmol) of 2-chloro-6-amino-9-[3,5-di-O-(4-chlorobenzoyl)-2-deoxy-β-D-ribofuranosyl]-purine and 0.01% (0.027 g, 0.05 mmol) of 2-chloro-6-trimethylsilylamino-9-[3,5-di-O-(4-chlorobenzoyl)-2-deoxy-β-D-ribofuranosyl]-purine.

EXAMPLE 3

Preparation of 2-chloro-2'-deoxy-adenosine (Cladribine)

To the above prepared mixture of 2-chloro-6-trimethylsilylamino-9-[3,5-di-O-(4-chlorobenzoyl)-2-deoxy-β-D-ribofuranosyl]-purine (IVa) and 2-chloro-6-amino-9-[3,5-di-O-(4-chlorobenzoyl)-2'-deoxy-β-D-ribofuranosyl]-purine (IVb) (179 g, >95.4% HPLC purity) in MeOH (895 mL, 5 P) was added 29% MeONa/MeOH solution (5.25 g, 0.1 eq.) at 20-30° C. The mixture was stirred at 20-30° C. for 6 hours, the solid was filtered, washed with MeOH (60 mL, 0.34 P) and then dried in vacuo at 50° C. for 6 hour to give 72 g white to off-white crude cladribine with 98.9% HPLC purity in ca. 93% yield.

EXAMPLE 4

Recrystallisation

Crude cladribine (70 g), $H_2O$ (350 mL, 5 P), MeOH (350 mL, 5 P) and 29% MeONa/MeOH solution (0.17 g) were stirred and heated under reflux until the mixture turned clear. The mixture was stirred for 3 hour and was then filtered to remove the precipitates at 74-78° C. The mixture was stirred and heated under reflux until the mixture turned clear and was then cooled. Crystals started to form at ca. 45° C. The slurry was stirred for 2 hour at the cloudy point. The slurry was cooled slowly at a rate of 5° C./0.5 hour. The slurry was stirred at 10-20° C. for 4-8 hours and then filtered. The filter cake was washed three times with MeOH (50 mL each) and dried at 50° C. in vacuo for 6 hours to give 62.7 g of 99.9% HPLC pure cladribine in ca. 90% yield.

EXAMPLE 5

Preparation of 2-chloro-6-trimethylsilylamino-9-[3,5-di-O-(4-chlorobenzoyl)-2-deoxy-β-D-ribofuranosyl]-purine 2-Chloroadenine (2.2 Kg, 13.0 mol, 1.0 eq.), MeCN (20.7 Kg, 12 P), and BSTFA (10.0 Kg, 38.9 mol, 3.0 eq.) were stirred and heated under reflux for 3 hours and then filtered through celite and was cooled to about 60° C. TfOH (0.40 Kg, 2.6 mol, 0.2 eq.) and 1-O-acetyl-3,5-di-O-(4-chlorobenzoyl)-2-deoxy-D-ribofuranose (III; 5.87 Kg, 13.0 mol, 1.0 eq.) were added into the filtrate and the mixture was stirred at about 60° C. for 29.5 hours. The slurry was cooled to about 20° C. and stirred for 2 hours. The solids were filtered and washed with MeCN (2.8 Kg) twice and dried in vacuo at 60° C. to give 5.17 Kg with a 96.5% HPLC purity in 62% yield of a mixture of 2-chloro-6-trimethylsilylamino-9-[3,5-di-O-(4-chlorobenzoyl)-2-deoxy-β-D-ribofuranosyl]-purine (IVa), and non-silylated derivative 2-chloro-6-amino-9-[3,5-di-O-(4-chlorobenzoyl)-2'-deoxy-β-D-ribofuranosyl]-purine (IVb).

EXAMPLE 6

Preparation of 2-chloro-2'-deoxy-adenosine (Cladribine)

To a mixture of 25% sodium methoxide in MeOH (0.11 Kg, 0.5 mol, 0.1 eq.) and MeOH (14.8 Kg, 5 P) at about at 25° C. was added 2-chloro-6-trimethylsilylamino-9-[3,5-di-O-(4-chlorobenzoyl)-2-deoxy-β-D-ribofuranosyl]-purine (IVa) and non-silylated derivative 2-chloro-6-amino-9-[3,5-di-O-(4-chlorobenzoyl)-2'-deoxy-β-D-ribofuranosyl]-purine (IVb) (3.70 Kg, combined HPLC purity of >96.3%) and the mixture was agitated at about 25° C. for 2 hours. The solids were filtered, washed with MeOH (1.11 Kg, 0.4 P) and then dried in vacuo at 60° C. for 4 hours to give 1.43 Kg of a crude cladribine with 97.8% HPLC purity in ca. 87% yield.

EXAMPLE 7

Recrystallisation of Crude Cladribine

A mixture of crude cladribine (1.94 Kg, >96.0% HPLC purity), MeOH (7.77 Kg, 5 P), process purified water (9.67 Kg, 5 P) and 25% sodium methoxide in MeOH (32 g, 0.15 mol) were stirred and heated under reflux until the solids dissolved. The solution was cooled to about 70° C. and treated with activated carbon (0.16 Kg) and celite for 1 hour at about 70° C., rinsed with a mixture of preheated MeOH and process purified water (W/W=1:1.25, 1.75 Kg). The filtrate was cooled to about 45° C. and maintained at this temperature for 1 hours, and then cooled to about 15° C. and agitated at this temperature for 2 hours. The solids were filtered and washed with MeOH (1.0 Kg, 0.7 P) three times and were then dried in vacuo at 60° C. for 4 hours giving API grade cladribine (1.5 Kg, 5.2 mol) in 80% yield with 99.84% HPLC purity.

EXAMPLE 8

Recrystallisation of Crude Cladribine

A mixture of crude cladribine (1.92 Kg, >95.7% HPLC purity), MeOH (7.76 Kg, 5 P), process purified water (9.67 Kg, 5 P) and 25% sodium methoxide in MeOH (36 g, 0.17 mol) were stirred and heated under reflux until the solids dissolved. The solution was cooled to about 70° C. and treated with activated carbon (0.15 Kg) and celite for 1 hour at about 70° C., rinsed with a mixture of preheated MeOH and process purified water (1:1.25, 1.74 Kg). The filtrate was cooled to about 45° C. and maintained at this temperature for 1 hour, and then cooled to about 15° C. and agitated at this temperature for 2 hours. The solids were filtered and washed with MeOH (1.0 Kg, 0.7 P) three times and were giving damp cladribine (1.83 Kg). A mixture of this cladribine (1.83 Kg), MeOH (7.33 Kg, 5 P) and process purified water (9.11 Kg, 5 P) were stirred and heated under reflux until the solids dissolved and was then cooled to about 45° C. and maintained at this temperature for 1 hours. The slurry was further cooled to about 15° C. and agitated at this temperature for 2 hours. The solids were filtered and washed with MeOH (0.9 Kg, 0.7 P) three times and were then dried in vacuo at 60° C. for 4 hours giving API grade cladribine (1.38 Kg, 4.8 mol) in 75% yield with 99.86% HPLC purity.

What is claimed is:

1. A process of purifying cladribine comprising:
   a) dissolving crude solid cladribine in a protic solvent and water in the presence of a base to form a solution, wherein the crude solid cladribine and the solution both comprise protected or partially protected nucleoside impurities;
   b) maintaining the solution at an elevated temperature so that the solution is homogeneous until the amount of protected or partially protected nucleoside impurities in the solution is reduced to a pre-determined upper limit;
   c) cooling the solution of step b) so that crystals of cladribine are formed and isolated.

2. The process of claim 1 wherein the protic solvent is methanol, and the base is NaOMe.

3. The process of claim 1 wherein the pre-determined upper limit is 0.10% by HPLC analysis.

4. The process of claim 1 wherein prior to step a), the process comprises:
   1) treating a mixture comprising a compound of formula IV and at least one undesired isomer with a sulfonic acid based Lewis or Brønsted acid in an organic solvent and in the presence of a silylating agent so that the at least one undesired isomer isomerizes and converts to the compound of formula IV, wherein the compound of formula IV has the following chemical formula:

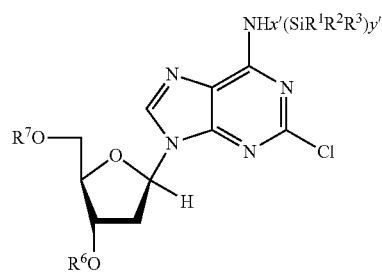

IV wherein each of $R^1$, $R^2$ and $R^3$ is independently alkyl, alkenyl, alkynyl or aryl, x' is 0, 1 or 2 y' is 2, 1 or 0, each of $R^6$ and $R^7$ is independently a hydroxyl protecting group;

2) isolating the compound of formula IV from the mixture obtained in step 1);
   3) converting the compound of formula IV to cladribine to obtain a reaction mixture comprising cladribine; and
   4) obtaining the crude solid cladribine by isolating cladribine from the reaction mixture obtained in step 3).

5. The process of claim 4 wherein the organic solvent is MeCN.

6. The process of claim 1 wherein prior to step a), the process comprises:
   (a') coupling a compound of formula II

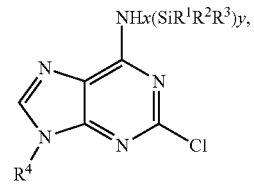

II wherein $R^4$ is hydrogen or $SiR^1R^2R^3$, x is 0, 1 or 2, y is 2, 1 or 0, respectively, and
when $R^4$ is hydrogen, y is 2 or 1; with a protected 2-deoxy-ribofuranose of formula III

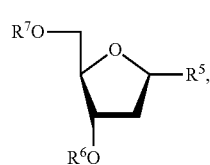

III wherein $R^5$ is a leaving group, in an organic solvent and in the presence of a sulfonic acid based Lewis or Brønsted acid to obtain a compound of formula IV:

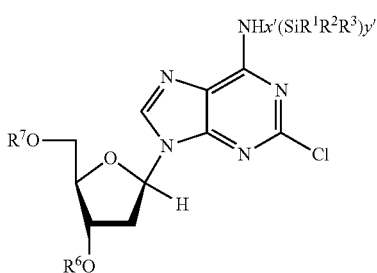

IV wherein each of $R^6$ and $R^7$ is independently a hydroxyl protecting group, each of $R^1$, $R^2$ and $R^3$ is independently alkyl, alkenyl, alkynyl or aryl, x' is 0, 1 or 2, y' is 2, 1 or 0;

(b') converting the compound of formula IV to cladribine to obtain a reaction mixture comprising cladribine; and (c') obtaining the crude solid cladribine by isolating cladribine from the reaction mixture obtained in step (b').

\* \* \* \* \*